United States Patent [19]
Weiss

[11] Patent Number: 5,623,926
[45] Date of Patent: Apr. 29, 1997

[54] HANDHELD ELECTROCARDIOGRAM MONITOR WITH ELECTRODES MOUNTED ON SWING ARMS

[75] Inventor: David M. Weiss, Centerville, Ohio

[73] Assignee: Technology Transfer, Inc., Lafayette, Ind.

[21] Appl. No.: 487,029

[22] Filed: Jun. 7, 1995

[51] Int. Cl.[6] .................................................. A61B 5/0408
[52] U.S. Cl. ........................................................... 128/639
[58] Field of Search ....................... 607/36, 37; 128/639, 128/696, 701, 710, 712; D24/167, 168

[56] References Cited

U.S. PATENT DOCUMENTS

| | | | |
|---|---|---|---|
| 3,989,038 | 11/1976 | Neward | 128/696 |
| 4,130,022 | 12/1978 | Goodrich et al. | 128/660.1 |
| 4,606,352 | 8/1986 | Geddes et al. | 128/702 |
| 5,022,410 | 6/1991 | Hall et al. | 128/639 |

OTHER PUBLICATIONS

"High-Tech Medicine 'Star Trek' Technology Yields Human Benefits," by Bea Northcott, Nineveh, IN. Article in Oct., 1988 edition of *Purdue Alumnus;* pp. 12, 13, 26, 27 and 33.

Primary Examiner—William E. Kamm
Assistant Examiner—George R. Evanisko
Attorney, Agent, or Firm—Woodard, Emhardt, Naughton, Moriarty & McNett

[57] ABSTRACT

A handheld electrocardiogram monitor with electrodes mounted on swing arms which are rotatably mounted on the bottom case of the ECG monitor housing, to which the swing arms are frictionally engaged and also engaged by means of a detent mechanism which includes a combination of detent grooves and ball spring plungers. The grooves are provided with 60° spacing on standoffs mounted on the swing arm, and the ball plungers are mounted on the bottom case of the monitor in positions 90° apart about the rotational axis. The 60° phasing of the grooves combines with the 90° spacing of the plungers to provide 30° indexing.

7 Claims, 4 Drawing Sheets

HANDHELD ELECTROCARDIOGRAM MONITOR WITH ELECTRODES MOUNTED ON SWING ARMS

BACKGROUND OF THE INVENTION

This invention relates to equipment for monitoring the electrical activity of the heart in a living body, and particularly to portable electrocardiogram monitors.

A number of portable devices exist for monitoring the electrical activity of the heart. Examples of the same are disclosed in U.S. Pat. No. 4,606,352 to Geddes et al., which patent is hereby incorporated by reference. This patent discloses the use of dry electrodes mounted directly on one side of an ECG monitor housing with an LCD display on the opposite side of the housing for visual display of an ECG waveform. While this device is very useful during emergency medical diagnosis and in other situations where an immediate record of the ECG is desired, the fixed position of the electrodes relative to the display imposes an undesirable limitation in terms of the available viewing angle for a user of the device.

SUMMARY OF THE INVENTION

The present invention provides a handheld electrocardiogram monitor with a swing arm assembly which allows for variable positioning of the sensing electrodes relative to the display, resulting in a configuration more beneficial to the desired function of the device. Furthermore, the shape of the swing arm assembly accommodates the human anatomy by allowing the sensing electrodes to contact the skin surface around curved surfaces. More specifically, the swing arm rotates with respect to the main case so that the user of the device can manipulate the viewing angle for ease in reading the LCD display. The swing arm is held fixed in its rotational position to some degree by means of a friction clutch. Additionally, the device includes a detent mechanism which provides indexed rotation of the swing arm with respect to the case, preferably with indexing every 30° of a rotational range of motion of 180°.

In the preferred embodiment the detent mechanism includes a cylindrical shaft affixed to the swing arm assembly and provided with grooves at 60° intervals about its circumference, and two spring ball plungers affixed to the case of the ECG monitor and spaced 90° apart about the circumference of the shaft in a position to engage the grooves in the shaft.

The advantages of the present invention will become more apparent upon reading the following detailed description in conjunction with the accompanying drawings.

DESCRIPTION OF THE PREFERRED EMBODIMENT

Figure 1:
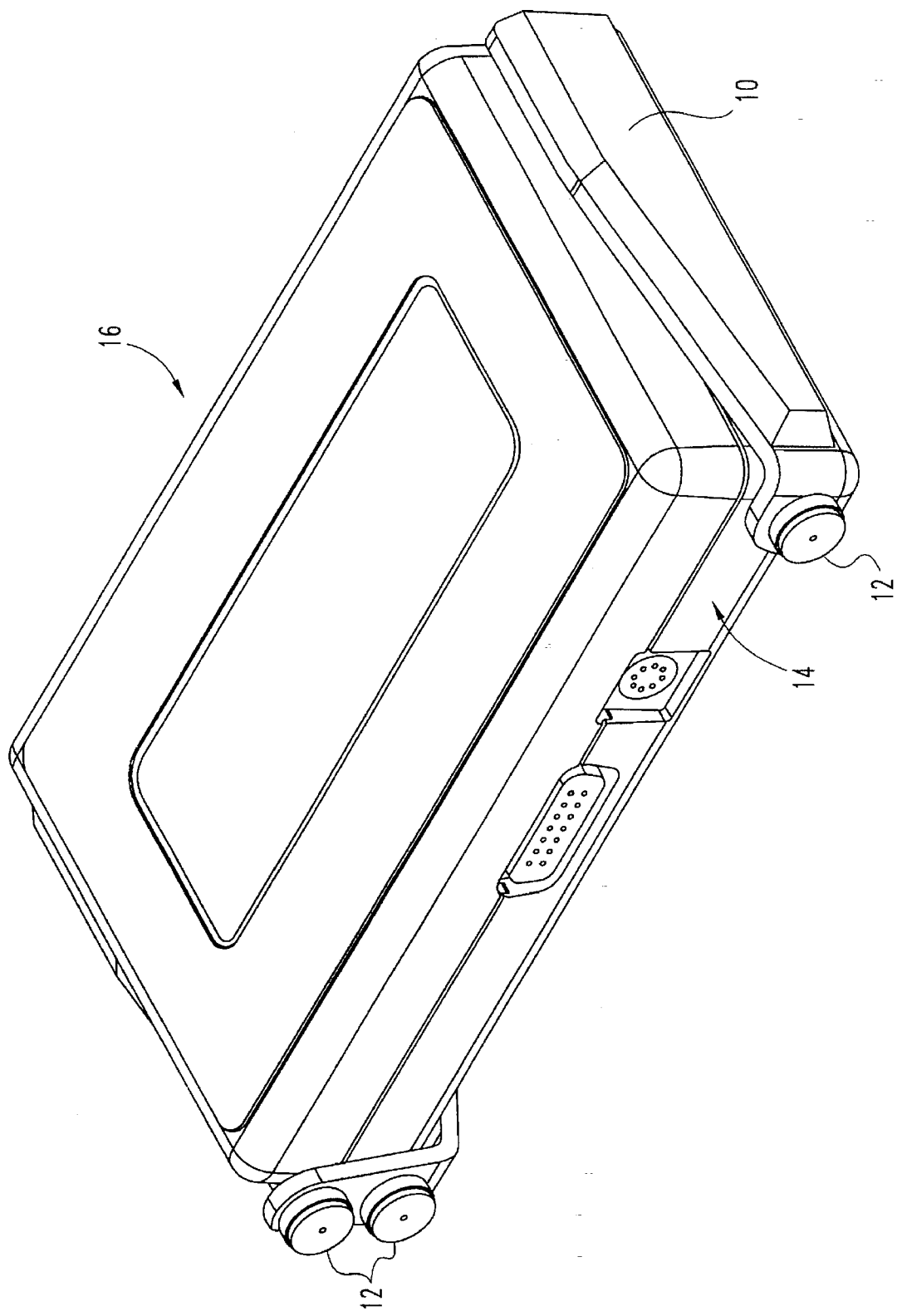
FIG. 1 is a perspective view of the preferred embodiment of an ECG monitor with electrodes mounted on swing arms according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
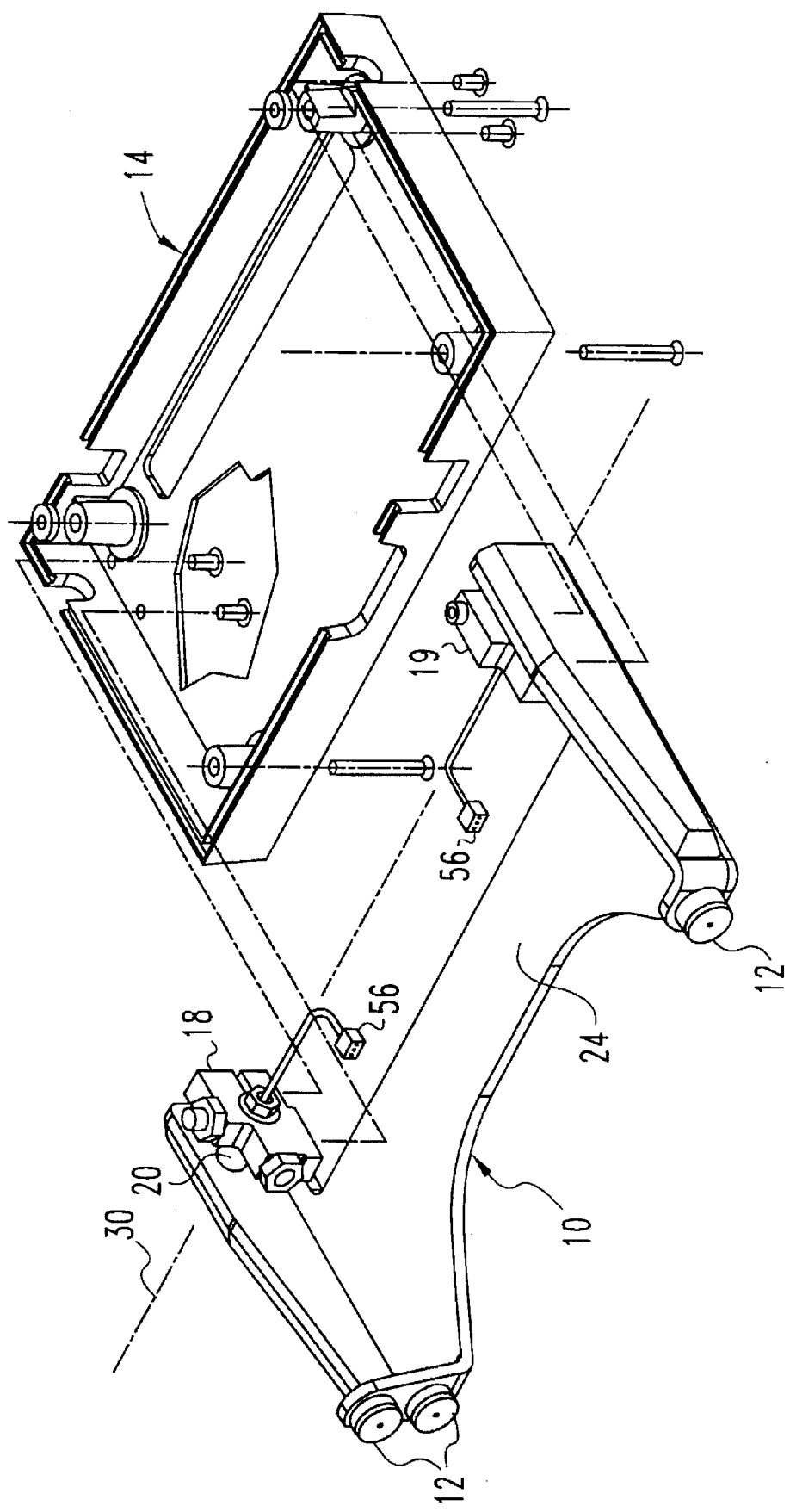
FIG. 2 is a partially exploded view illustrating the mounting configuration of the swing arm assembly relative to the bottom case of the ECG monitor of FIG. 1.
Figure 3:
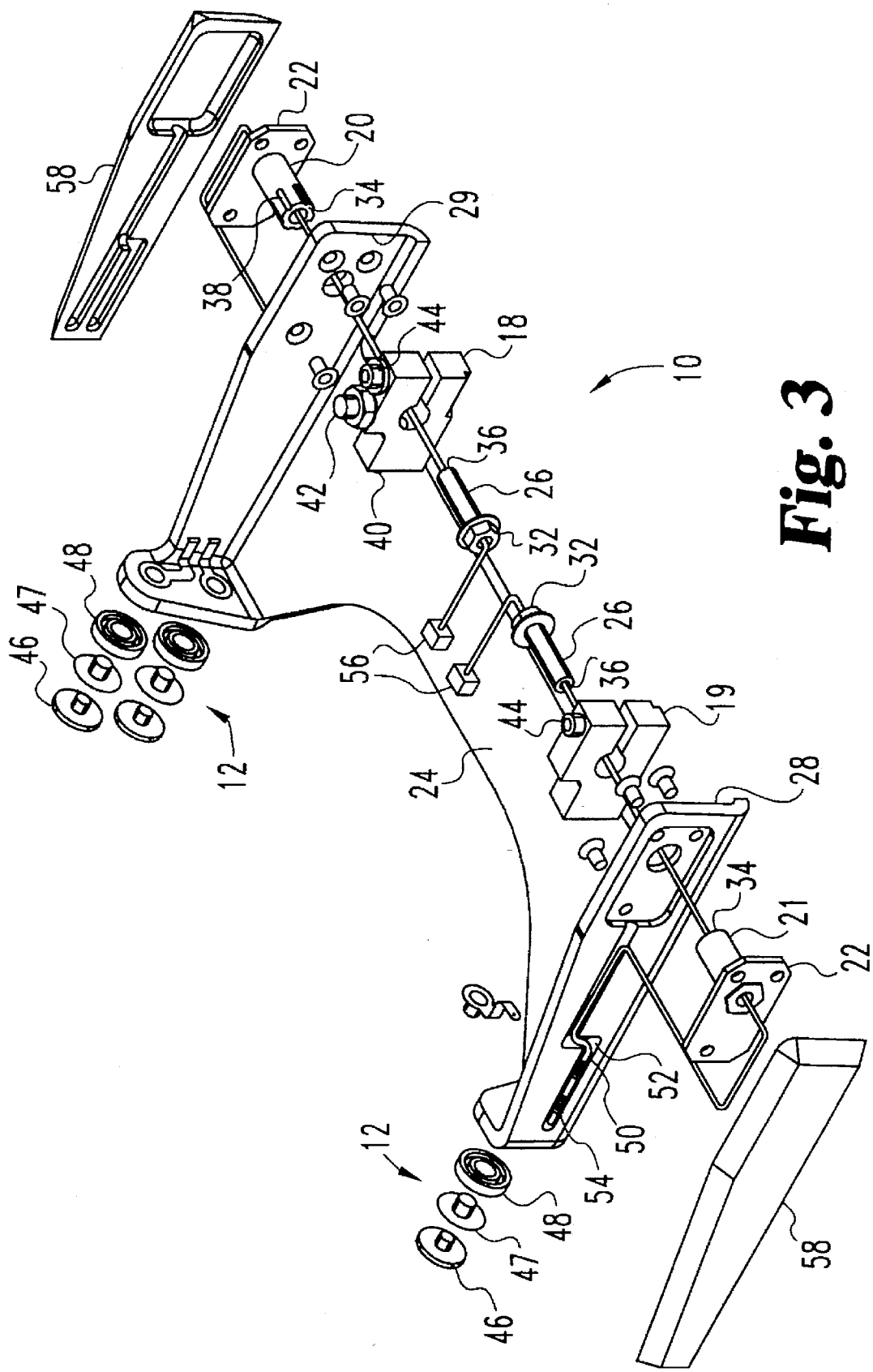
FIG. 3 is an exploded view of the swing arm assembly of FIG. 2.

With combined reference to FIGS. 1–3, the swing arm assembly 10 with electrodes 12 mounted thereon is rotatably mounted on the bottom case 14 of the housing of an ECG monitor 16 on an axis defined by a pair of clutch clamps 18 and 19 affixed to the bottom case by screws or otherwise in a conventional manner, and by a corresponding pair of cylindrical standoffs 20 and 21 rotatably mounted within the clutch clamps. The standoffs are pressed into aluminum support plates 22 which are in turn attached to the swing arm chassis 24 by screws or other conventional fastening means for structural support. The standoffs are hollow and are internally threaded to receive pivot screws 26 which are also hollow. Pivot screws 26 screw into the standoffs and cooperate with the standoffs to fix the lateral location of the swing arm assembly relative to the case, maintaining a constant gap of preferably 0.060" between the case 14 and each side wall 28 and 29 of the swing arm chassis 24. Chassis 24, which is preferably thermoformed polycarbonate, is formed with a spacing between its two side walls 28 and 29 along rotational axis 30 which is greater than the maximum dimension of the ECG monitor case along that same axis by an amount, preferably 0.120", which provides the desired gap between the swing arm chassis and device case when the device is fully assembled.

The standoffs are internally threaded to receive their respective pivot screws, which when assembled are secured tightly to their respective standoffs with the undersides of the screw heads 32 flush with the inside end surfaces 34 of their respective standoffs. The opposite end 36 of each pivot screw is also flush with its respective standoff and with its respective support plate. Details of the interconnection of the pivot screws, standoffs and respective clutch clamps are shown in FIG. 4.

Figure 4:
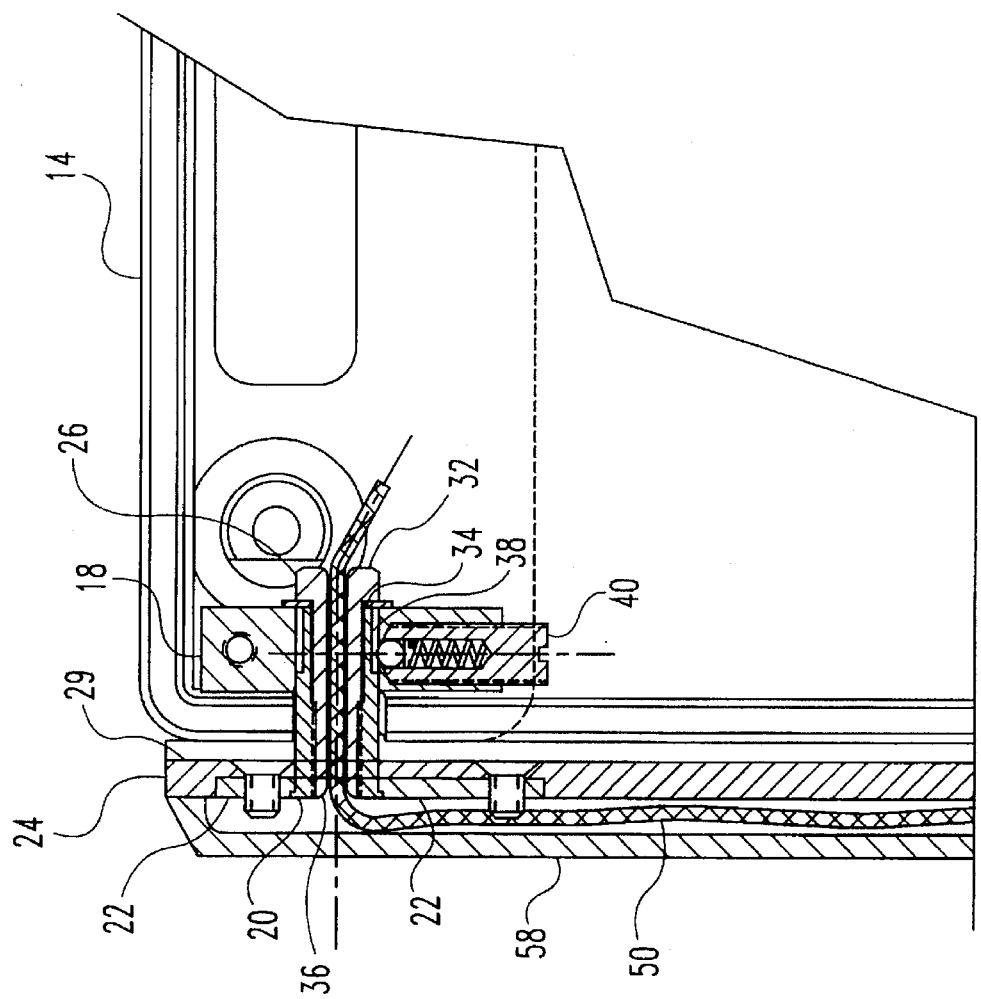
FIG. 4 is a top sectional view of a portion of the swing arm assembly.

The outer ends 36 of the pivot screws are provided with a smooth radius as shown in FIG. 4 to allow for the 90° bend in the conductors without appreciable wear. Nylon is a suitable material for the pivot screws, although brass is preferred for strength and ease of machining. Brass with a polished surface at least on the rounded ends 36 is especially preferred for minimizing wear on the conductors.

The detent mechanism provides for indexing of the swing arm in 30° increments throughout its 180° of rotational freedom. This is accomplished by machining one of the two standoffs with grooves 38 which are spaced 60° apart as illustrated in FIG. 3. Spring-loaded ball plungers 40 and 42 are screwed into clutch clamp 18 and engage with the grooves in the corresponding standoff 20. To achieve 30° indexing, two ball plungers are fixed 90° apart, one mounted horizontally as shown in FIG. 3 and in greater detail in FIG. 4, and the other mounted vertically and directly above the rotational axis as shown in FIG. 3. These two ball plungers engage the grooves on the standoff, in which the first detent is rotationally located with the swing arm in a closed position. The disclosed phasing of the grooves and plungers is particularly advantageous due to the limited circumferential distance around the standoff.

The clutch clamps, which are preferably formed of polyethylene, are attached to the case bottom and are used for lateral support of the swing arm, as described above, and also provide rotational friction, which is adjustable by means of screws 44 which are provided to tighten the clamps. Thus, tactile support is provided to the user by means of friction in addition to the detent mechanism.

The electrodes 12 include three pieces 46, 47 and 48, the outermost of which 46 contacts the skin and is preferably ABS thermoplastic plated with 0.1 mil thick silver/silver chloride. The outermost piece, or eyelet, is pressed into a female snap 47 which is snapped into a socket 48 which has been riveted to the polycarbonate chassis by a custom formed eyelet. For field replacement, the female snap/eyelet assembly is easily removed from the socket 48.

The electrodes are connected to internal circuitry within the ECG monitor by means of three conductors 50, i.e., one for each electrode, which are preferably miniature coaxial cable. Slots 52 are provided in the side walls of the swing arm chassis for the coaxial cables and for input resistors 54 connected on the electrode end of each coaxial cable. The cables are routed from the resistors through the slots provided in the swing arm and then through the centers of the standoff/pivot screw assemblies, which are made hollow for this purpose. The coaxial cables are terminated in connectors 56 on a circuit board (not shown) within the ECG monitor. The coaxial cables are hidden with cover plates 58 which are preferably solvent bonded to the outside on both sides of the chassis.

The electronic circuitry for the ECG monitor may be of the type disclosed in the above-referenced U.S. Pat. No. 4,606,352 to Geddes et al., which patent is hereby incorporated by reference.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A handheld electrocardiogram monitor, comprising:

a housing;

a swing arm rotatably mounted on said housing, said swing arm having a plurality of electrodes mounted thereon;

an ECG monitor circuit contained within said housing and connected to said electrodes on said swing arm; and a detent mechanism attached to said swing arm and said housing, said detent mechanism including a first member having a plurality of grooves therein spaced apart by a first dimension, and a plurality of groove-engaging elements spaced apart by a second dimension different from said first dimension.

2. The handheld electrocardiogram monitor of claim 1, wherein said first member is a cylindrical shaft having grooves spaced 60° apart about its circumference, and wherein said groove-engaging elements are spring-loaded ball plungers positioned 90° apart about the circumference of said cylindrical shaft.

3. The handheld electrocardiogram monitor of claim 2, wherein said plungers are affixed to said housing and said shaft is affixed to said swing arm.

4. The handheld electrocardiogram monitor of claim 3, further comprising an electrical conductor connected between said ECG monitor circuit and one of said electrodes, and a hollow pivot screw secured to said shaft, wherein said shaft is hollow, and wherein said electrical conductor extends through said hollow shaft and said hollow pivot screw.

5. The handheld electrocardiogram monitor of claim 4, further comprising a clutch clamp mounted on said housing, wherein said shaft is rotatably mounted within said clutch clamp, said clutch clamp including means for frictionally engaging said shaft.

6. The handheld electrocardiogram monitor of claim 1, further comprising an electrical conductor connected between said ECG monitor circuit and one of said electrodes, wherein said first member is hollow, and wherein said electrical conductor extends through said hollow first member.

7. The handheld electrocardiogram monitor of claim 1, further comprising a clutch clamp mounted on said housing, wherein said first member is rotatably mounted within said clutch clamp, said clutch clamp including means for frictionally engaging said first member.

* * * * *